United States Patent
Ryan

(10) Patent No.: US 10,034,740 B2
(45) Date of Patent: Jul. 31, 2018

(54) COVERED STENT

(75) Inventor: Michael Ryan, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/169,715

(22) Filed: Jun. 27, 2011

(65) Prior Publication Data

US 2011/0319980 A1 Dec. 29, 2011

Related U.S. Application Data

(60) Provisional application No. 61/359,128, filed on Jun. 28, 2010.

(51) Int. Cl.
| | |
|---|---|
| A61F 2/82 | (2013.01) |
| A61F 2/07 | (2013.01) |
| A61F 2/04 | (2013.01) |
| A61F 2/90 | (2013.01) |
| A61F 2/95 | (2013.01) |

(52) U.S. Cl.
CPC .......... *A61F 2/07* (2013.01); *A61F 2/90* (2013.01); *A61F 2002/044* (2013.01); *A61F 2002/045* (2013.01); *A61F 2002/072* (2013.01); *A61F 2002/9534* (2013.01); *A61F 2230/0078* (2013.01); *A61F 2250/0018* (2013.01); *A61F 2250/0039* (2013.01)

(58) Field of Classification Search
CPC ...... A61F 2/82; A61F 2/86; A61F 2/88; A61F 2/90
USPC .......... 623/1.11–1.16; 606/194, 198
See application file for complete search history.

(56) References Cited

U.S. PATENT DOCUMENTS

| | | | | |
|---|---|---|---|---|
| 5,575,818 | A * | 11/1996 | Pinchuk | A61F 2/90 606/195 |
| 8,764,813 | B2 * | 7/2014 | Jantzen et al. | 623/1.13 |
| 2002/0188344 | A1 * | 12/2002 | Bolea et al. | 623/1.11 |
| 2006/0217799 | A1 * | 9/2006 | Mailander | A61F 2/91 623/1.44 |
| 2007/0179590 | A1 * | 8/2007 | Lu et al. | 623/1.16 |
| 2009/0182413 | A1 * | 7/2009 | Burkart et al. | 623/1.16 |
| 2010/0161033 | A1 * | 6/2010 | Jantzen et al. | 623/1.16 |

FOREIGN PATENT DOCUMENTS

WO  WO 97/25002  7/1997

* cited by examiner

*Primary Examiner* — Tuan V Nguyen
(74) *Attorney, Agent, or Firm* — Brinks Gilson & Lione

(57) ABSTRACT

A covered stent having a selected arrangement of uncovered cells is provided. The uncovered cells are configured to provide a desired flexibility profile to the stent structure. In one preferred embodiment, the stent contains one or more circumferential rows of uncovered cells located between two or more circumferential rows of covered cells. In some embodiments, the stent may have a central body portion and one or more flanges where the circumferential rows of uncovered cells may be located within the flange(s).

5 Claims, 4 Drawing Sheets

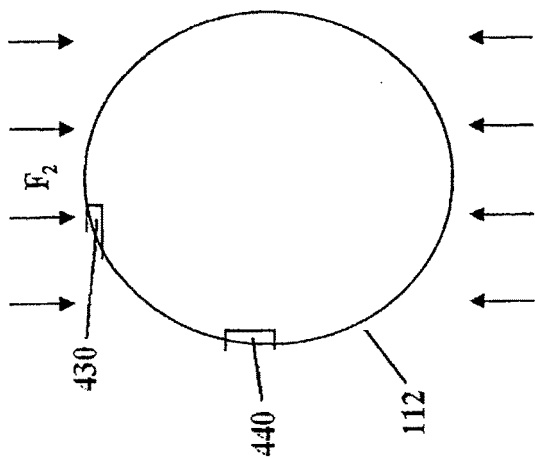
FIG. 4C
FIG. 4D
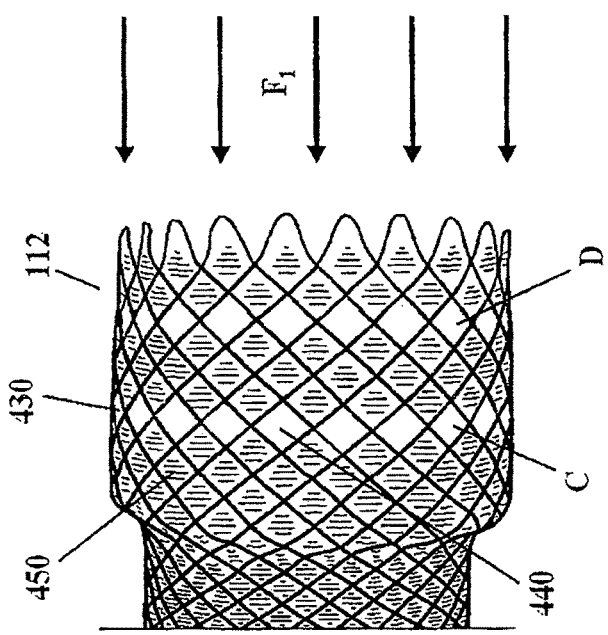
FIG. 4A
FIG. 4B

COVERED STENT

This application claims priority to U.S. Provisional Application Ser. No. 61/359,128, filed Jun. 28, 2010.

TECHNICAL FIELD

The present disclosure relates generally to medical devices, and more particularly to covered stents.

BACKGROUND

Stents are medical devices commonly used to maintain patency of body vessels, such as those of the vascular and gastrointestinal systems. Stents are often delivered via a minimally invasive procedure and thereafter expanded to contact and support the inner wall of the targeted vessel. In general, most stents include a tubular shaped support structure having a plurality of interstices configured to facilitate compression and expansion of the stent.

In some instances, it is advantageous for a stent to include a covering over its support structure. Esophageal stents, for example, are often encased in a silicone membrane to prevent tumor ingrowth and overgrowth, to seal fistulas, and to reduce food impaction as well as tissue perforation. Covered stents are generally available in one of two configurations—fully or partially covered. A fully covered stent typically includes a continuous membrane over the entire surface of the stent structure. A partially covered stent may include membrane covering over a central portion of the structure but have uncovered ends or flanges. Fully covered stents may be preferred where there is a high risk of tumor ingrowth or overgrowth, or where there is need to seal fistulae. However, because tissue is generally unable to grow into fully covered stents, they are prone to proximal and distal migration subsequent to implantation. The membrane covering also makes the stent more rigid, which further contributes to migration incidence because the encased structure may not sufficiently adapt to temporary changes in lumen shape (e.g., from external trauma or peristaltic motion). Partially covered stents are generally more flexible than their fully covered counterparts and therefore may better respond to such changes. The partial cover design also allows a certain amount of tissue ingrowth, better securing the stent at the site of implantation. Excessive tissue ingrowth and overgrowth can, however, lead to a loss of the stent's functionality and may complicate or entirely prevent stent repositioning or removal. Partially covered stents are also generally ineffective at sealing or mitigating formation of fistulae in the portions lacking membrane coverage.

Whether a fully covered or partially covered stent is selected for a particular procedure often depends on the organ targeted, the particular characteristics of the diseased vessel, the patient's needs, and on physician preference. Despite the aforementioned options, there exists a need for stents that incorporate the advantages of fully and partially covered stents but lack or mitigate the disadvantages of each. In particular, there is need for a covered stent that can prevent excessive tissue ingrowth/overgrowth similar to a fully covered stent, but possess sufficient flexibility to adapt to changes in lumen shape similar to a partially covered stent.

SUMMARY

The present disclosure generally provides a covered stent having a selected distribution of uncovered cells configured to impart a desired flexibility profile to the stent structure. In one embodiment, a stent configured for implantation in a body lumen includes a tubular framework having a plurality of cells arranged into circumferential rows along a longitudinal axis of the framework. At least one of the circumferential rows of cells lacks a membrane covering and is located between two or more circumferential rows of cells having a membrane covering. A circumferential row of uncovered cells may be bordered on both sides by two circumferential rows of cells having the membrane covering. The stent may include a central body portion and one or more flanges. The flange may include a circumferential row of cells lacking the membrane covering, which may be bordered on both sides by two circumferential rows of cells having the membrane covering. Where the stent includes at least two circumferential rows of uncovered cells, the rows may be aligned adjacent one another. Alternatively, the rows may be separated by one or more circumferential rows of membrane covered cells. The stent may include a central body portion that extends longitudinally between two flanges, wherein every cell in the central body portion may be a covered cell and each of the first and second flanges may include at least one circumferential row of cells lacking the membrane covering. Within each of the flanges, the circumferential rows may be adjacent or consecutively aligned, or may be separated by one or more circumferential rows of membrane covered cells.

In another embodiment, an implantable medical device is provided that includes a tubular body having a plurality of interstices. The tubular body is expandable from a radially compressed configuration to an expanded configuration. A membrane covers a plurality of the interstices. However, at least one group of the interstices lacks the membrane covering, wherein the group is bordered on at least two sides by membrane covered interstices. The group may be one of a circumferential, longitudinal, or helically oriented row of interstices. The group may include two or more immediately adjacent uncovered interstices and may be repeated as a pattern in the tubular body.

In another embodiment, a braided stent is provided that includes a plurality of membrane covered circumferential rows of cells and a plurality of uncovered circumferential rows of cells. The uncovered circumferential rows of cells are located between at least two circumferential rows of membrane covered cells. The uncovered circumferential rows of cells may be bordered on each side by a circumferential row of membrane covered cells. At least one of the uncovered circumferential rows of cells may completely circumscribe the stent. Optionally, the stent may include a central body portion and a flange including at least one uncovered circumferential row of cells.

Other devices, systems, methods, features and advantages will be, or will become, apparent to one with skill in the art upon examination of the following figures and detailed description. It is intended that all such additional devices, systems, methods, features and advantages be included within this description, and be protected by the following claims.

BRIEF DESCRIPTION OF THE DRAWINGS

The system may be better understood with reference to the following drawings and description. The components in the figures are not necessarily to scale, with emphasis instead being placed upon illustrating the principles of the present disclosure. Moreover, in the figures, like referenced numerals designate corresponding parts throughout the different views.

FIGS. 4A-4D depict longitudinal and radial compression of a stent flange having two circumferential rows of uncovered cells.

DETAILED DESCRIPTION

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

Devices and Systems

Figure 1:
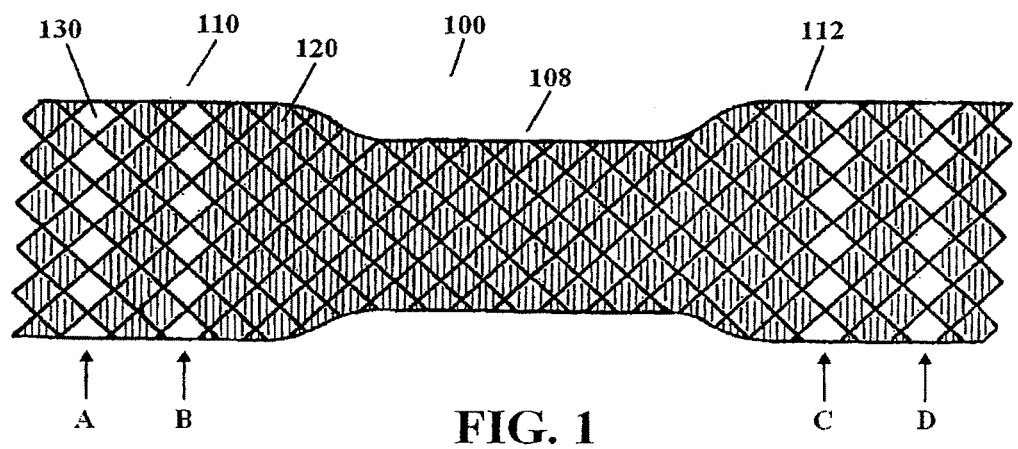
FIG. 1 depicts a covered stent including circumferentially oriented rows of uncovered cells.

FIG. 1 depicts a self-expanding stent 100 having a framework or structure comprised of one or more helically wound or braided filaments. Intersections of filament in the braid pattern create a plurality of closed, rhombus shaped cells or interstices defined at their perimeter by the filament(s). The framework formed by the filaments includes a tubular shaped central body portion 108 extending longitudinally between two flanges 110 and 112. As will be described in greater detail below, the stent framework includes a plurality of membrane covered or coated cells and a selected arrangement of uncovered cells configured to impart a desired flexibility profile to the stent structure.

Figure 2:
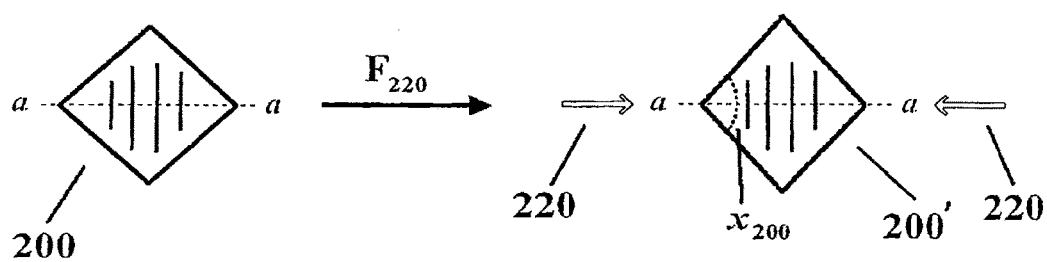
FIG. 2 depicts deformation of a covered cell by an external force.
Figure 3:
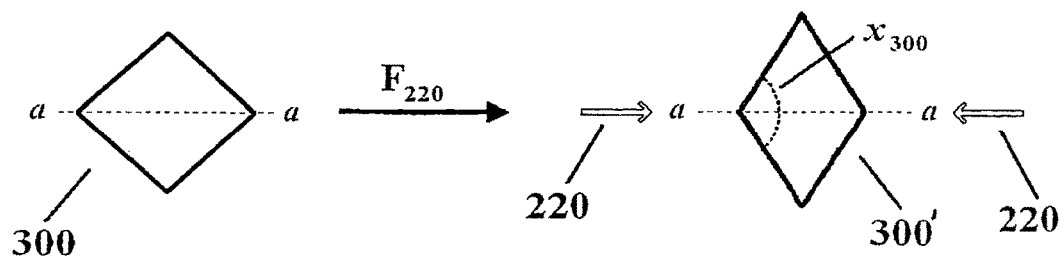
FIG. 3 depicts deformation of an uncovered cell by an external force.

In one exemplary embodiment, all of the cells within central body portion 108 and a plurality of the cells in flanges 110 and 112 include a membrane covering or coating. A selected number of the cells in flanges 110 and 112 lack the membrane covering. For example, cell 120 includes a membrane covering whereas cell 130 lacks the covering. Cells that lack a membrane covering may be referred to herein as "uncovered cells" or "soft cells." As shown in FIG. 1, the uncovered cells are arranged into four circumferential rows A-D circumscribing the flanges. Cells that lack a membrane covering are generally more flexible than the covered cells because the membrane covering adds resistance to movement of the filaments bordering the membrane covered cells. By way of example, FIGS. 2 and 3 illustrate the effect of applying an external force 220 to two cells 200 and 300, wherein each cell differs only in that cell 300 lacks a membrane covering. When force 220 is applied to each cell along axis a-a, the cells may adopt a flexed configuration, such as 200' and 300' as shown. Soft cell 300 undergoes a greater shape distortion relative to covered cell 200 such that 300' has an internal angle $x_{300}'$>cell 200' internal angle $x_{200}'$.

Thus, as an axially directed force is applied to stent 100, from peristaltic motion for example, the circumferential rows of soft cells may deform in shape or flex in response to the force to a greater extent than will the covered cells. This increased flexibility may reduce the incidence of stent migration as well as tissue damage caused by interaction of the stent with the surrounding tissue. However, because stent 100 is substantially covered with membrane—aside from the soft cell rows—the stent may be less prone to tissue ingrowth and overgrowth relative to a partially covered stent of the same structural configuration. Further, stent 100 can be used to effectively seal fistulae (e.g., a tracheoesophageal fistula) to a greater extent than would a partially covered stent of the same structural configuration.

A force that acts in parallel or in the same plane as a soft cell, particularly along one of the two axes defined by intersection of filament (e.g., axis a-a), may cause maximum deformation or flexing of the cell. In contrast, a force that acts perpendicularly or out of plane with a cell will generally cause comparatively less, if any, deformation of the cell shape. Thus, a longitudinal force may act upon all or a substantial portion of the soft cells in a flange whereas a radial force will act upon only certain soft cells in the circumferential rows. FIGS. 4A-4D depict the effect of applying longitudinally and radially directed external forces to flange 112. When longitudinally directed force $F_1$ is applied to the stent, as depicted in FIG. 4A, soft cell rows C and D may uniformly flex in response, exemplified by the deformation of soft cells 430 and 440 in FIG. 4B. Covered cells such as 450 may also deform in shape, but generally less so than the soft cells. When a radially directed force $F_2$ is applied to the flange (FIG. 4C), the force acts in a direction perpendicularly to certain soft cells, such as cell 430, and parallel to others, such as cell 440. As a result, soft cell rows C and D only partially compress in response to the radial force, as depicted in FIGS. 4C-4D. One advantage of this illustrated embodiment is that the flanges can adapt to peristaltic motion of a vessel, but maintain sufficient radial force against the vessel wall.

Soft cells may be distributed throughout a stent structure in various patterns and rows. For example, a stent may include any selected number of circumferential rows of soft cells. A stent may include longitudinally or helically oriented rows of soft cells. Soft cells may be singularly distributed throughout a stent structure (i.e., a single soft cell bordered on all sides by covered cells), or may be distributed into groups of two or more into various rows or groupings. Soft cells may be distributed into identical symmetrical patterns at each end of a stent, or alternatively, each end or flange may include a soft cell distribution unique to the respective end. The selected number and distribution pattern of soft cells for a particular stent may depend on factors such as size of the stent, the desired flexibility profile, the targeted anatomy, and the particular needs of the patient.

Figure 5A:
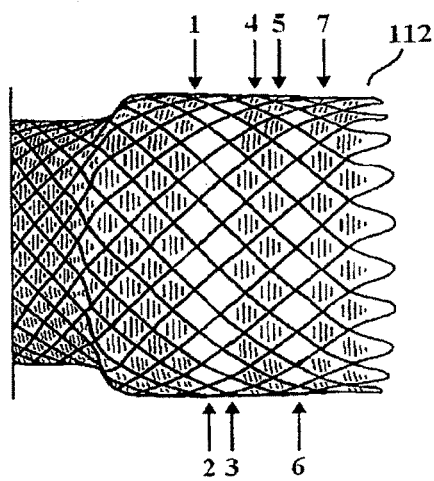
FIGS. 5A-5F depict alternate soft cell distributions in a stent structure.
Figure 5B:
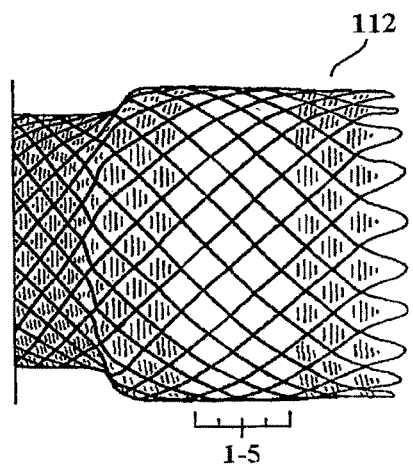
Figure 5C:
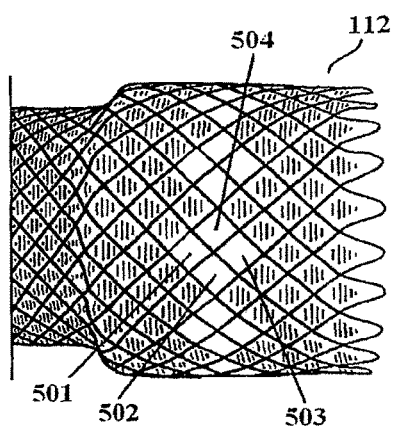
Figure 5D:
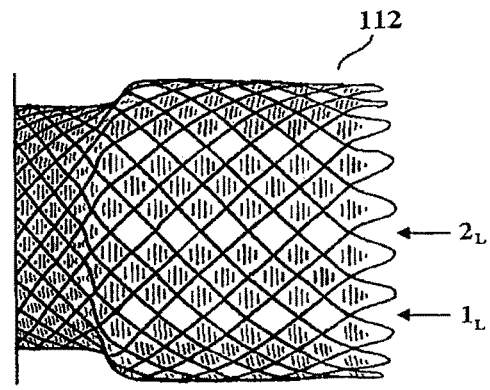
Figure 5E:
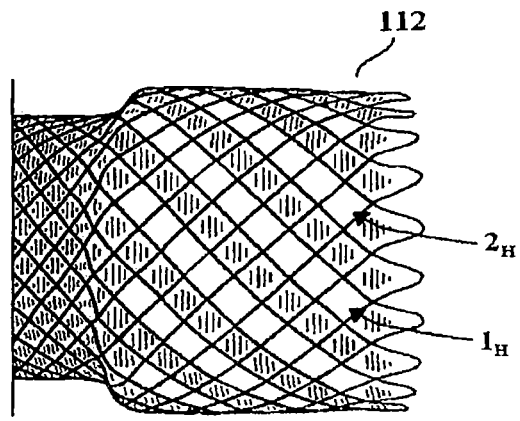
Figure 5F:
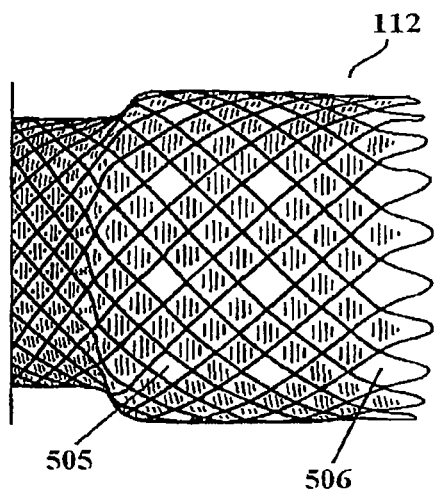

FIGS. 5A-5F depict exemplary alternative embodiments of soft cell distributions. FIG. 5A depicts flange 112 including three circumferential rows of soft cells 2, 3 and 6 between covered rows 1 and 7, among others. Rows 2 and 3 are immediately adjacent (i.e., share a border) whereas row 6 is bordered by covered rows 5 and 7. FIG. 5B depicts the flange including a group of circumferential rows of soft cells 1-5 wherein the rows are bordered by at least one other circumferential row of soft cells in the group (e.g., row 3 is bordered by rows 2 and 4). FIG. 5C depicts the flange including a repeating group of four soft cells 501-504 wherein the pattern circumscribes the flange. FIG. 5D depicts the flange including longitudinally oriented rows of soft cells, such as rows $1_L$ and $2_L$. FIG. 5E depicts the flange including helically oriented rows of soft cells, such as rows $1_H$ and $2_H$. FIG. 5F depicts the flange including single soft cells distributed throughout the flange, wherein the internal soft cells, such as cell 505, are bordered on all four sides by membrane covered cells. The uncovered absolute end cells, such as cell 506, are bordered by two covered cells. Although several exemplary embodiments have been described, other soft cell distributions are possible. In one preferred embodiment, a stent includes soft cells arranged into one or more circumferential rows circumscribing the stent, such as depicted in FIGS. 1 and 4.

Any suitable biocompatible material may be used as the membrane covering. Preferably, the membrane covering is an elastic or flexible material that can adapt to radial compression of a stent prior to delivery, as well as foreshortening of a stent during expansion from a compressed state. Suitable membrane materials include, for example, silicones (e.g. polysiloxanes and substituted polysiloxanes), polyurethanes, thermoplastic elastomers, polyolefin elastomers, polyethylene, polytetrafluoroethylene, nylon, and combinations thereof. In one preferred embodiment, the membrane covering comprises silicone. In certain embodiments, where the stent will be implanted at or near an acidic environment (e.g., will be exposed to gastric fluids), preferably the membrane covering is resistant to acid degradation.

The membrane covering may be applied to a stent by any suitable method as is known in the art. For example, the membrane may be applied by spraying, dipping, painting, brushing, or padding. Generally, the membrane covering or coating has a thickness ranging from about 0.0025 mm to about 2.5 mm, from about 0.01 mm to about 0.5 mm, or from about 0.03 mm to about 0.07 mm. The thickness of the membrane may be selected, for example, by controlling the number of dips or passes made during the application process. In one exemplary embodiment, a braided stent may be dipped in silicone liquid, removed, and thereafter cured. Preferably, the coating extends over the abluminal and luminal surfaces of the filaments, and also resides in the cells or interstices defined by the filament braid pattern. In certain embodiments, the coating may be selectively applied to the luminal or abluminal surfaces of the stent structure such that the coating residing within the cells is biased to the luminal or abluminal surface of the stent structure. After the membrane has been applied to the stent structure, soft cells may be created by manually removing the silicone from the selected cells with an appropriate tool. For example, devices such as needles and forceps may be used to remove membrane material from selected cells to create a desired pattern of soft cells. In an alternative embodiment, the soft cells in the stent pattern may fabricated by covering or shielding certain cells prior to application of the membrane coating. For example a segment of shrink wrap comprising polytetrafluoroethylene may be applied to a circumferential row of cells by placing a piece of the material at the desired location and thereafter heat shrinking in place. With the selected cells shielded, the membrane material may be applied and cured, and the shrink wrap thereafter removed. This procedure may minimize or eliminate the need for manual removal of silicone from selected cells.

Prior to applying the membrane, a stent may be polished, cleaned, and/or primed as is known in the art. A stent may be polished, for example, with an abrasive or by electropolishing. A stent may be cleaned by inserting the stent into various solvents, degreasers and cleansers to remove any debris, residues, or unwanted materials from the stent surfaces. Optionally, a primer coating may be applied to the stent prior to application of the membrane covering or coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure.

Although the illustrated embodiments depict a stent having a central body portion and two flanges, other stent configurations are possible. For example, a stent may include a single flange, two asymmetrically shaped flanges, or may entirely lack flanges and instead have a uniform or substantially uniform diameter along the entire length of the stent. A stent may include a uniform diameter along the length of the stent but include slightly flared proximal and/or distal ends. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of antegrade and retrograde migration. Preferably, the flanges are sized and shaped to accommodate the vessel or organ of implantation. For example, stents destined for lower esophageal implantation may have differently shaped and sized flanges compared to a stent designed for upper esophageal implantation. Further, the flanges may be atraumatically shaped to reduce incidence of tissue perforation and overgrowth. For example, the absolute ends of the flanges may curve or bend inward toward the stent lumen to minimize tissue damage at or near the stent ends. In certain embodiments, a stent may include other design elements configured to secure the stent at the site of implantation. For example, in certain embodiments, a stent may include small anchors, hooks, or barbs that will anchor the stent to the internal wall of the targeted body lumen. In other embodiments, the stent may be sutured to the site of implantation at one or more portions of the stent structure.

A stent may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at an intersection of filament in the braid pattern. In certain embodiments, a stent may include four radiopaque markers with two markers affixed to a first flange and two to a second flange. Optionally, radiopacity can be added to a stent through coating processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

A stent may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible materials, such as for example, stainless steel, suture materials or other polymeric materials such as polyethylene, ultra-high molecular weight polyethylene, polyester, nylon, or the like. Optionally, the lasso may be coated with a material, such as polytetrafluoroethylene, to reduce frictional interactions of the lasso with surrounding tissue.

Stents including soft cells may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents are often used in vessels that are subject to changes in shape and/or changes in position, such as those of the peripheral and gastrointestinal systems. Peripheral vessels regularly change shape as the vessels experience trauma from external sources (e.g, impacts to arms, legs, etc.); and many gastrointestinal vessels naturally change shape as peristaltic motion advances food through the digestive tract. One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization of the lumen as well as working channels through which devices and instruments may be delivered to the site of implantation. A fluoroscope also provides visualization of the patient anatomy to aid in placement of an implantable device, particularly in the gastrointestinal system.

Mechanically expandable stents (e.g., balloon expandable stents) are generally made from plastically deformable materials (e.g., 316L stainless steel) and thus can be crimped and delivered in a reduced diameter and thereafter expanded to a precise expanded diameter. Balloon expandable stents are often used to treat stenosed coronary arteries. One common procedure for implanting a balloon expandable stent involves mounting the stent circumferentially on a balloon-tipped catheter and threading the catheter through a vessel passageway to the target area. Once the balloon is positioned at the targeted area, the balloon may be inflated to dilate the vessel and radially expand the stent. The balloon may then be deflated and removed from the passageway.

Expandable stents according to the present disclosure may be formed by any suitable method as is known in the art. In certain embodiments, the expandable stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments or wires may be of various cross-sectional shapes. For example, the filaments or wires may be flat in shape or may have a circular-shaped cross-section. The filaments or wires may have any suitable diameter, such as for example, from about 0.10 to about 0.30 mm. As will be described in greater detail below, the expandable stents may formed from a variety of biocompatible materials. For example, the filaments or wires may comprise one or more elastically deformable materials such as shape memory alloys (e.g., 304 stainless steel, nitinol, and the like).

Alternatively, expandable stents may be formed from metallic or polymeric sheets or tubular blanks. For example, a stent framework comprising a selected pattern of struts defining a plurality of cells or interstices may be fabricated by subjecting a metallic or polymeric sheet or tubular blank to laser cutting, chemical etching, high-pressure water etching, mechanical cutting, cold stamping, and/or electro discharge machining. After obtaining a sheet of cut, etched or machined material with the appropriate strut pattern, the sheet may be rolled into a tubular shape to form the stent framework. The stent framework may also be machined from a tubular blank, thereby eliminating the need for a rolling step.

A stent may be made from any suitable biocompatible material(s). For example, a stent may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

A stent may be fabricated to any suitable dimensions. A stent having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

A stent according to the present disclosure may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., Evolution™ Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

While various embodiments of the presently disclosed stent have been described, it will be apparent to those of ordinary skill in the art that many more embodiments and implementations are possible within the scope of the present disclosure. Accordingly, the disclosure is not to be restricted except in light of the attached claims and their equivalents.

The invention claimed is:

1. A self-expanding braided stent, comprising:
a central body portion disposed between a pair of flanges, the pair of flanges each having an expanded diameter greater than an expanded diameter of the central body portion;
a plurality of fully membrane covered circumferential rows of cells, wherein the membrane comprises a flexible non-biodegradable material biased in an expanded cell configuration and configured to permit both full radial expansion of the stent and contact against a vessel wall of a bodily lumen upon initial deployment thereof within the bodily lumen; and
a plurality of fully uncovered circumferential rows of cells, wherein the fully uncovered circumferential rows of cells are located between at least two circumferential rows of fully membrane covered cells, and wherein at least one of the fully uncovered circumferential rows of cells completely circumscribes each of the flanges of the stent.

2. The stent of claim 1, wherein the fully membrane covered circumferential row of cells does not prevent expansion of the stent.

3. The stent of claim 1, wherein, upon initial deployment, the membrane is configured to permit radial expansion of the stent into contact against the vessel wall of the bodily lumen.

4. The stent of claim 1, wherein the plurality of fully uncovered circumferential rows of cells comprises at least two adjacent fully uncovered circumferential rows of cells completely circumscribing the stent.

5. The stent of claim 4, wherein the at least two fully uncovered circumferential rows of cells completely circumscribing the stent are bordered on each side by a circumferential row of membrane covered cells.

* * * * *